(12) United States Patent
Stergiopoulos et al.

(10) Patent No.: US 8,834,376 B2
(45) Date of Patent: Sep. 16, 2014

(54) DISPERSIVE ULTRASOUND TECHNOLOGY AS A DIAGNOSTIC DEVICE FOR TRAUMATIC BRAIN INJURIES

(75) Inventors: Stergios Stergiopoulos, Toronto (CA); Andreas Freibert, Toronto (CA); Jason Zhang, Toronto (CA)

(73) Assignee: Her Majesty The Queen in right of Canada as Represented by The Minister of Health, Ottawa, Ontario (CA)

( * ) Notice: Subject to any disclaimer, the term of this patent is extended or adjusted under 35 U.S.C. 154(b) by 233 days.

(21) Appl. No.: 13/407,378

(22) Filed: Feb. 28, 2012

(65) Prior Publication Data

US 2013/0225998 A1 Aug. 29, 2013

(51) Int. Cl.
 *A61B 8/00* (2006.01)
 *A61B 8/08* (2006.01)
 *A61B 5/00* (2006.01)

(52) U.S. Cl.
 CPC ........ *A61B 8/0808* (2013.01); *G01N 2291/048* (2013.01); *A61B 5/4064* (2013.01); *A61B 8/0858* (2013.01)
 USPC ............ 600/448; 600/438; 600/451; 73/597; 73/1.82

(58) Field of Classification Search
 CPC .. A61B 8/0816; A61B 8/1808; A61B 8/0858; G01N 2291/048
 See application file for complete search history.

(56) References Cited

U.S. PATENT DOCUMENTS

| | | | |
|---|---|---|---|
| 5,596,508 A * | 1/1997 | Cuffe | 702/171 |
| 6,587,796 B2 * | 7/2003 | Fukuhara | 702/45 |
| 6,644,119 B1 | 11/2003 | Sinha | |
| 6,719,696 B2 | 4/2004 | Stergiopoulos | |
| 6,912,891 B2 | 7/2005 | Coupland | |
| 6,959,601 B2 | 11/2005 | Sinha | |
| 7,114,375 B2 | 10/2006 | Panetta | |
| 7,140,239 B2 | 11/2006 | Greenwood | |
| 7,228,740 B2 | 6/2007 | Sinha | |
| 7,331,233 B2 | 2/2008 | Scott | |
| 7,736,314 B2 * | 6/2010 | Beach et al. | 600/437 |
| 7,739,911 B2 | 6/2010 | Panetta | |
| 7,803,112 B2 | 9/2010 | Kwon | |
| 7,854,701 B2 | 12/2010 | Stergiopoulos | |
| 7,874,991 B2 | 1/2011 | Chiang | |
| 7,878,062 B2 | 2/2011 | Wrobel | |
| 7,894,663 B2 | 2/2011 | Berg | |
| 7,901,357 B2 | 3/2011 | Boctor | |

(Continued)

OTHER PUBLICATIONS

Dispersive Ultrasound Technology as a Diagnostic Device for Traumatic Brain Injuries,Stergios Stergiopoulos,PH.D. et al.;Jun. 2011,NATO-HFM-207.

(Continued)

*Primary Examiner* — Jonathan Cwern
*Assistant Examiner* — Amanda Lauritzen Moher
(74) *Attorney, Agent, or Firm* — Michael R. Williams; Ade & Company Inc.

(57) ABSTRACT

Described herein is the use of ultrasound pulses at different frequencies to track the dispersion properties of intracranial tissues which may have been altered due to traumatic or other neurological brain injury. Dispersive ultrasound does not provide imaging, but it can provide data of significant diagnostic value by using decision support systems that can be trained as a medical diagnostic system for traumatic brain injuries applications to detect specific patterns of dispersion that are associated with specific intracranial injuries.

11 Claims, 9 Drawing Sheets

(56) References Cited

U.S. PATENT DOCUMENTS

| | | |
|---|---|---|
| 7,912,258 B2 | 3/2011 | Warmath |
| 7,912,528 B2 | 3/2011 | Krishnan |
| 8,013,991 B2 * | 9/2011 | Maier et al. .................. 356/301 |
| 8,498,828 B2 * | 7/2013 | Sasaki ............................ 702/45 |
| 2002/0143479 A1 * | 10/2002 | Fukuhara ....................... 702/45 |
| 2006/0079782 A1 * | 4/2006 | Beach et al. .................. 600/450 |
| 2007/0056374 A1 * | 3/2007 | Andrews ....................... 73/628 |
| 2008/0287803 A1 | 11/2008 | Li |
| 2010/0027569 A1 | 2/2010 | Brekke |
| 2010/0152579 A1 | 6/2010 | Lin |
| 2011/0218742 A1 * | 9/2011 | Sasaki ............................ 702/45 |

OTHER PUBLICATIONS

Non-Invasive Monitoring of Vital Signs and Traumatic Brain Injuries, Stergios Stergiopoulos et al.; Defence R&D Canada, Technical Report, DRDC TR 2008-105; Jul. 2008.

An Experimental Evaluation of Split-Beam Processing as a Broadband Bearing Estimator for Line Array Sonar Systems, Stergios Stergiopoulos et al., Received May 20, 1996; accepted for publication Jul. 3, 1997; Acoustical Society of America.

Non-Invasive Measurement Technologies, Nimtech SonicGauge-Technology Overview.

* cited by examiner

DISPERSIVE ULTRASOUND TECHNOLOGY AS A DIAGNOSTIC DEVICE FOR TRAUMATIC BRAIN INJURIES

BACKGROUND OF THE INVENTION

Traditional diagnostic methods require information from medical imaging technologies and chemical analysis of bodily fluids. Medical imaging technologies such as Magnetic Resonance Imaging (MRI), Computed Tomography (CT), Positron Emission Tomography (PET) or Ultrasound scans can provide highly detailed geometrical information about a patient's internal organs. They accomplish this by mapping out the geometrical distribution of internal tissues or fluid. It is widely used for diagnosing physical illness such as tumours or injuries. Chemical analysis of biological samples can provide detailed information about chemical composition within the body.

The drawback of medical imaging, however, is that it provides only geometric information but contains little information about composition. Chemical and/or biological analysis on the other hand provides composition but not geometry. Certain illnesses, such as traumatic brain injuries, are often difficult to detect with medical imaging as these injuries do not show any initial symptoms and can be hard to localize or deteriorate too fast for chemical analysis, thus making it difficult to treat many patients effectively. The present invention proposes the use of dispersive ultrasound as a non-invasive diagnostic system for traumatic brain injury.

In general, ultrasound refers to longitudinal mechanical waves with high frequencies in the range of MHz. Ultrasound systems have traditionally been used for medical or industrial imaging, wherein ultrasound reflection points are mapped out in order to build up an internal image of the target. These systems return information about the internal structure of a target but not its composition.

Dispersion is an effect in which the non-linear, frequency-dependent bulk modulus of the medium results in different propagation speeds for different sound frequencies. Since the properties of the bulk modulus depend on the specific characteristics of the medium, such as density, composition, mixture concentration, distribution and in some situations chemical composition, the pattern of frequency-dependent propagation speeds can be used to identify the medium. In other words, the dispersive effect is the result of different propagation speeds for different frequencies. As can be seen in Equations (1) and (2), the propagation speed $c(f)$ as a function of frequency has a dependency on elasticity $K_v$ for liquid media and the bulk modulus $K_B$ for solid media.

$$c(f) = \sqrt{\frac{K_v(f)}{\rho_0 \cdot \beta_{ad}}} \quad \text{for liquid media} \tag{1}$$

$$c(f) = \sqrt{\frac{K_B(f)}{\rho_0}} \quad \text{for solid media} \tag{2}$$

Thus, a Dispersive Ultrasound System (DUS) measures the ultrasound dispersion patterns of different media and uses these patterns for identification. A DUS utilizes ultrasound pulses of different frequencies to interrogate a medium in order to provide propagation times for each of the transmitted frequencies. This process provides estimates of the dispersion patterns $c(f)$ for a specific contained medium. Since each medium has a unique bulk modulus, a DUS can identify unknown contained media by matching the dispersion pattern of the unknown sample with a previously established library of dispersion patterns of known media.

The observed changes to the propagation speed are usually very small and require a very precise measurement of the propagation speed. Instead of measuring the speed of sound in the media, it is easier to accurately measure the propagation time of ultrasound signals that travel along a known distance from a transmitter T to a receiver R, as depicted in FIG. 1.

As shown by Equation (3), the propagation speed $c(f)$ can be estimated from the propagation time $t(f)$ by assuming that the constant dimension d, is known.

$$c(f) = \frac{d}{t(f)} \tag{3}$$

One way to very accurately measure the propagation time $t(f)$ required for the signal to travel from the transmitter to the receiver is by using a very high sampling frequency for the received signal. To achieve the necessary accuracy, however, a sampling frequency in the GHz range would be necessary. Such a system would be formidably expensive and have unacceptable power requirements for a portable device. Instead, we observe that an ultrasound signal is not only described by its frequency but also by phase information:

$$x(t) = A \cdot \sin(2\pi f \cdot t + \phi) \tag{4}$$

Therefore, to overcome the requirement for a high sampling frequency, the phase information of the ultrasound wave can be used along with its amplitude to provide accurate estimates of propagation times.

It is commonly known that the phase information only covers a range from $-\pi$ to $+\pi$. Hence, it can only be used to get additional information about one period of the signal. Beyond that, this information keeps repeating itself. Using a phenomenon from wave theory called beat-note, which is the result of the combination of two acoustic continuous wave signals that are close in pitch but yet not identical. The difference in frequency generates the beating. The frequency of the beat-note is given by:

$$f_{beat} = f_1 f_2 \tag{5}$$

The closer $f_1$ and $f_2$ are, the lower is the resulting frequency $f_{beat}$ and the longer is the period of the resulting beat phase $T_{beat} = 1/f_{beat}$. The use of the beat-note approach allows for the unique identification of a certain point in the signal. Once this unique point has been found, the phase information of the individual frequency can be used to accurately calculate propagation times.

Phase information is not limited by the sample rate, and therefore can provide nanosecond scale precision using sample rates only in the megahertz range. The complication with this approach however is the need to resolve the phase ambiguity problem, arising from the fact that phase information wraps around for every change in propagation time greater than a single period in the signal, as was discussed in the previous section.

An early approach (Stergiopoulos et al., 2008, "Non-invasive monitoring of vital signs and traumatic brain injuries", Defence R&D Canada—Toronto, Department of National Defence, (Technical Report), DRDC Toronto, TR 2008-105; U.S. Pat. No. 7,854,701) to solving the phase ambiguity problem used two closely spaced component frequencies to create a pair of high and low side image frequencies, that is, when the product of the two component frequencies are taken, they produce a new signal that is made up of two component signals, each with frequencies and phase at the sum and difference of the component frequencies:

$$\sin(2\pi f_1 + \phi_1)\sin(2\pi f_2 + \phi_2) = \quad (6)$$
$$\frac{(\cos(2\pi(f_1 - f_2) + (\phi_1 - \phi_2)) - \cos(2\pi(f_1 + f_2) + (\phi_1 + \phi_2))}{2}$$

The two resulting frequencies are called the high side image frequency ($f_1+f_2$) and the low side image frequency ($f_1-f_2$); and they should satisfy Eq. (7), which requires also a variable sampling rate. With a small enough frequency difference between the component frequencies, each cycle of the low side image frequency could span the entire transmission and reception pulse of the component signals. It was assumed that the frequencies of the component signals would be close enough that dispersive effects between them would be negligible. The phase position of the low side image frequency could then be used to match each cycle in the transmitted signal to its counterpart in the received signal, therefore solving the phase ambiguity problem.

$$\frac{f_t}{f_s} \neq \frac{m}{n}; \text{ with } m, n \in N \quad (7)$$

It was later determined that there is a reciprocal relationship between the frequency spacing of the component signals and the accuracy and sensitivity of the low side image signal's phase information.

As the frequency difference becomes smaller, the period of the low side image signal grows larger relative to the component signals' period, increasing the precision required in marking its phase. Furthermore, since the phase of the low side image signal is directly related to the phase difference of the component frequencies, any slight dispersion will cause the image signal to shift in phase by the same amount. Compounded with the increased precision requirement, the negligible dispersion assumption does not translate into negligible error, and phase ambiguity can not be resolved reliably with this method under all dispersion conditions.

In other words, the previous method described in Stergiopoulos et al., 2008 and U.S. Pat. No. 7,854,701 was based upon the beat-note and the assumption that the dispersive effect is negligible for the two component frequencies. However, simple simulations can show that this assumption is very limited. As an example, let us consider two signals with frequencies $f_1$=4.33333 MHz and $f_2$=4.6666666 MHz are used. According to Equation (5), the beat time for these two frequencies is 3 µs. Assuming there is no dispersion in the propagation speed of the ultrasound signals, then for this example c=1540 m/s. The resulting beat phase is shown in FIG. 2. Furthermore, it is assumed that the zero crossing of the beat phase is the point the system uses to calculate the time. Bushong and Archer (Bushong and Archer, 1991, "Diagnostic Ultrasound", Mosby Inc,) define the speed of sound for an aqueous human haemoglobin solution as:

$$c_{(f)} = (1523.83 + 0.4013 \cdot \log(f))\frac{m}{s} \quad (8)$$

The difference in speed for the two above frequencies results is then:

$$\Delta c_{(f)} = (1523.83 + 0.4013 \cdot \log(4.3 \times 10^6))\frac{m}{s} - \quad (9)$$
$$(1523.83 + 0.4013 \cdot \log(4.6 \times 10^6))\frac{m}{s} = 12.3\frac{m}{s}$$

If now the speed of sound only changes by 5 m/s for the frequency $f_2$, the resulting beat information changes to the one shown in FIG. 2. As a result, the initially used calibration point has moved into a completely different period than it was before. The error of this method grows with the bandwidth used and prevents the acquisition of reliable data sets. This may have an impact in providing reliable diagnosis, as discussed herein.

SUMMARY OF THE INVENTION

According to a first aspect of the invention, there is provided a method of identifying an unknown medium comprising:
  a) interrogating an unknown medium with a plurality of ultrasound pulses at different frequencies;
  b) identifying individual signals by pulse duration, center frequency and bandwidth;
  c) estimating the propagation time through the medium for a first ultrasound frequency using cross correlation;
  d) improving the estimate of the propagation time by determining zero phase crossing using linearity of phase;
  e) repeating steps (b)-(d) for all frequencies;
  f) using information derived from ultrasound pulses to generate an ultrasonic fingerprint of the medium; and
  g) identifying the medium based on characteristics of the fingerprint.

In some embodiments, the method includes at step (b) applying a temporal window to the signal.

The ultrasound signal may be a broadband frequency modulated signal.

Each signal may have a bandwidth of about 0.5 MHz.

Finite Impulse Response (FIR) filters may be applied to the cross correlation data.

The phase information may be calculated by Hilbert transformation.

The ultrasound fingerprint may be compared to a database of fingerprints of known media and the unidentified medium is identified based on said comparison.

The medium may be intracranial tissues.

The medium may be intracranial tissues which have been altered by a brain injury.

The database comparison may be carried out by a support vector machine.

DESCRIPTION OF THE PREFERRED EMBODIMENTS

Figure 1:
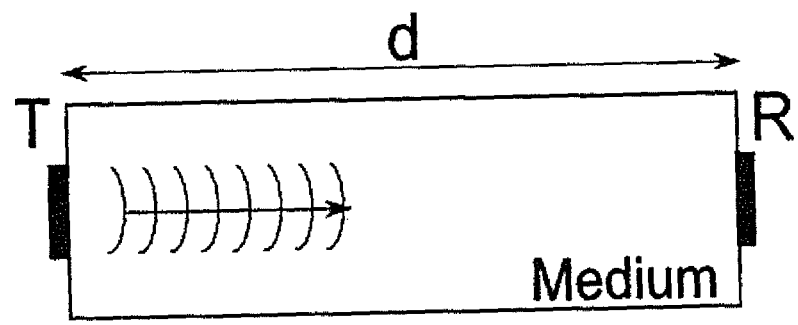
FIG. 1. Ultrasound signal traveling from transmitter T to receiver R in a medium with dimension d.
Figure 2:
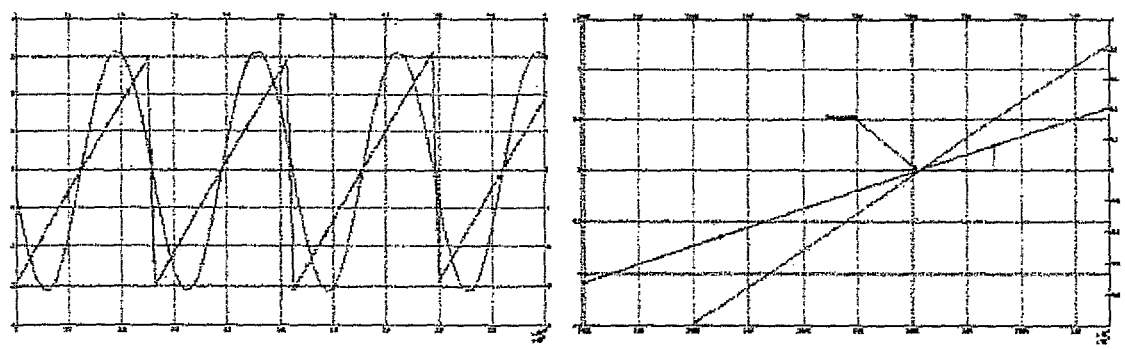
FIG. 2. Phase information along signal in time domain (left), detailed zero crossing.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Timely and rapid detection of non penetrating, closed Traumatic Brain Injury (TBI) remains a major challenge in military field operations. Mortality and morbidity from such injuries can be reduced if the injury is rapidly diagnosed and treated in far forward battalion medical aid stations and field hospitals, where sophisticated diagnostic tools are limited or not available. Exposure to blast pressure waves, for example, could result in injury to the brain that is not evident to external observation, and may go undetected. As such, there is a pressing need for portable diagnostic tools that can be deployed for early detection of neurological injury in front-line situations, where such injuries are most likely to occur.

Described herein is the use of ultrasound pulses at different frequencies to track the dispersion properties of intracranial tissues which may have been altered due to traumatic or other neurological brain injury. Dispersive ultrasound does not provide imaging, but it can provide data of significant diagnostic value by using decision support systems that can be trained as a medical diagnostic system for traumatic brain injuries applications to detect specific patterns of dispersion that are associated with specific intracranial injuries.

The core innovation for the present Dispersive Ultrasound System (DUS) is the signal processing configuration that provides estimates of the propagation time for signals of different frequencies. As stated in the previous section, highly accurate estimates of the signals' propagation times are required. This implies that simple time of arrival counting techniques are insufficient. Instead, chirping, phase measurement and new signal processing techniques have been used in a specific order that constitutes the core of the innovation to extract information from the signal in order to arrive at sub-sampling rate resolution. The current real time signal processing configuration of DUS contains four stages:
  a) Signal Generation and Transmission
  b) Propagation Time Estimation
   (i) Cross Correlation, estimates the propagation time to within one period
   (ii) Zero Phase Crossing, improves the propagation time estimate using linearity of phase
  c) Decision Support System.

According to an aspect of the invention, there is provided a method of identifying an unknown medium comprising:
  a) interrogating an unknown medium with a plurality of ultrasound pulses at different frequencies;
  b) identifying individual signals by pulse duration, center frequency and bandwidth;
  c) estimating the propagation time through the medium for a first ultrasound frequency using cross correlation;
  d) improving the estimate of the propagation time by determining zero phase crossing using linearity of phase;
  e) repeating steps (b)-(d) for all frequencies;
  f) using information derived from ultrasound pulses to generate an ultrasonic fingerprint of the medium; and
  g) identifying the medium based on characteristics of the fingerprint.

As discussed herein, in some embodiments, the method includes at step (b) applying a temporal window to the signal Preferably, the ultrasound signal is a broadband frequency modulated signal.

Preferably, each signal has a bandwidth of about 0.5 MHz although other suitable bandwidths may be used, as discussed herein.

As discussed herein, in some embodiments, Finite Impulse Response (FIR) filters are applied to the cross correlation data.

The phase information may be calculated by Hilbert transformation

The ultrasound fingerprint may be compared to a database of fingerprints of known media and the unidentified medium may be identified based on this comparison, as discussed herein.

In some embodiments, the medium is intracranial tissues. In yet other embodiments, the medium is intracranial tissues which have been altered by a brain injury or are suspected of having been altered by a brain injury, as discussed herein. In these embodiments, the frequencies may be between 500 kHz and 10 MHz.

As discussed below, the database comparison may be carried out by a support vector machine (SVM).

The dispersive ultrasound requires the transmission of signals at multiple frequencies in order to map out propagation delay characteristics. Several factors limit the frequencies that can be used. The first restriction is the signal attenuation and absorption in the medium to be measured. For most liquid media, almost all frequencies can propagate without significant attenuations; however, potential applications in heterogeneous media and brain impairment diagnostic applications restrict the frequencies to the range between 500-KHz and 10-MHz. As will be appreciated by one of skill in the art, the selection of the ultrasound frequencies is based on the absorption and dispersive properties of the interrogated medium and as such different frequency ranges may be used for the interrogation of different mediums.

Herein, the propagation time for each frequency is calculated independently and does not rely upon any information derived from other signals through a beat-note effect. To facilitate this calculation, the novel method uses broadband frequency modulated (FM) signals rather than monochromatic narrowband continuous wave (CW) signals as taught in U.S. Pat. No. 7,854,701. The bandwidth of the FM signal provides enough information to uniquely identify the beginning of a received signal. However, this new method also relies upon the estimation of the phase at a given sample point to increase the accuracy in the estimation process of the signal's propagation time.

The combined bandwidth of multiple frequencies can cover a range of a few megahertz. The information derived from these signals can then be used to generate a fingerprint of the medium, and this kind of fingerprint information can be used to classify a medium of interest as discussed herein.

Thus, the current algorithm is invariant to the sampling frequency and this approach for constant sampling frequency, for all the radiated FM signals, minimizes the complexity of the electronic design configuration.

Figure 3:
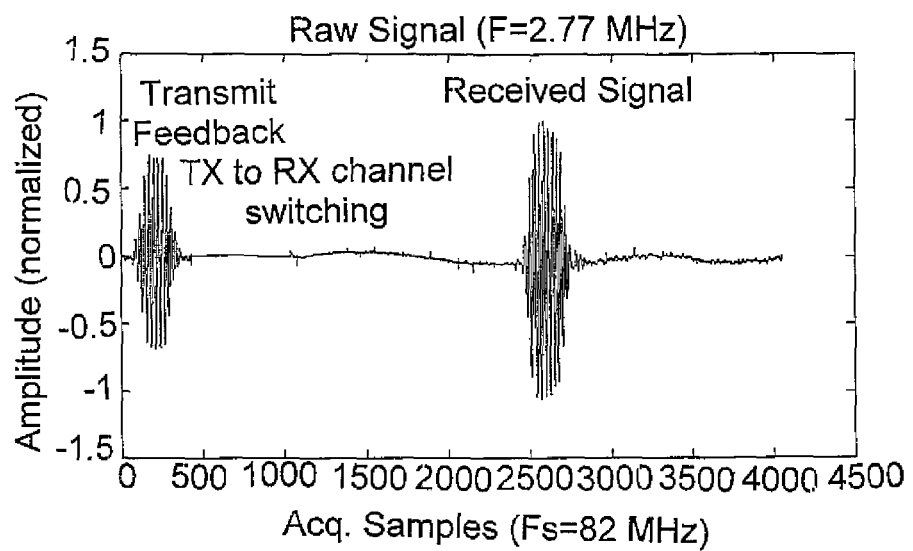
FIG. 3. Unfiltered transmit and receive signals.
Figure 4:
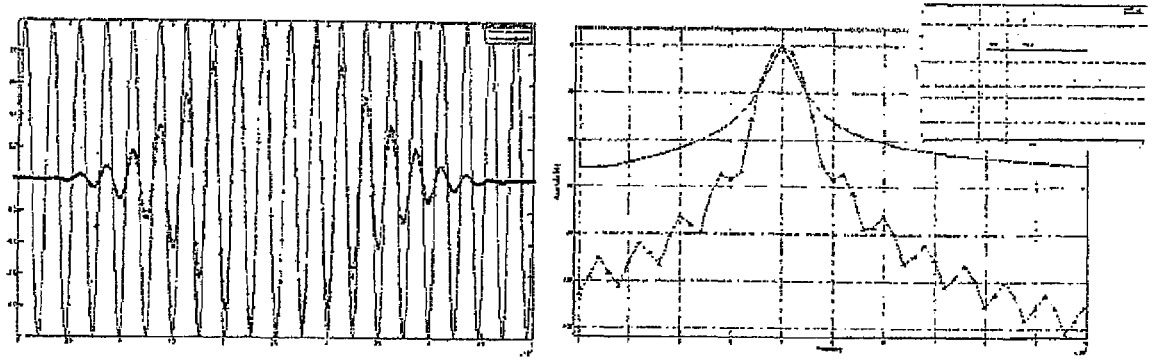
FIG. 4. Unwindowed and windowed Frequency Modulation (FM) signals in the time domain (left) and frequency domain (right).

The transmitted broadband signal is described by a number of parameters. These parameters are the pulse duration, the center frequency and its bandwidth. In order to reduce effects of harmonics, a temporal window is applied to the Frequency Modulated (FM) signal. At this point, it is important to note that the present invention is not restricted to FM type of signals and other types of broadband signals can be used as well. FIG. 3 shows the digitized unfiltered transmit and received signals and FIG. 4 shows a typical broadband transmit signal in Time and Frequency domains. In the Time domain, the amplitude of the windowed signal increases symmetrically slowly over time and reaches its maximum around the centre of the pulse. In the Frequency domain, the −3 dB bandwidth of the windowed signal is, as expected, more than twice the width of the unwindowed signal, but the side-lobe structure of the windowed signal is highly suppressed. In conclusion, the advantages of a windowed signal are that it has less energy in the side-lobes and a wider effective bandwidth in the region of interest.

As will be apparent to one of skill in the art, for unwindowed signals, there may be confusion in identifying the correct maximum peak of correlation output and therefore the estimates of the time delay (propagation time) may be wrong. Thus, windowed signals are much easier to use to identify the correct location of the maximum peak of the correlation output and therefore provide more accurate estimates of the propagation time.

Thus, each broadband radiated signal was chirped with an initial centre frequency in the range of 1.0 MHZ to 10-MHz and a bandwidth of 0.5 MHz, to allow for improved signal to noise ratio in the correlation process. As will be appreciated by one of skill in the art, the wider the signal bandwidth, the sharper and more narrow the width of the peak of the correlation output and the much more precise the propagation time estimates. For example, in an illustrative example, 500 KHz signal bandwidths that are centered at different frequencies in the range of 500 KHz to 10 MHz may be used. In this illustrative example, the selection of the centre frequencies is closely related with the transducer characteristics. For example, if two centre frequencies to be used are 3 MHz and 3.4 MHz then the two FM signals will be as follows: Broadband Signal-1: 2.75 MHz to 3.25 MHz with centered frequency 3 MHz; and Broadband Signal-2: 3.15 MHz to 3.65 MHz with centered frequency 3.4 MHz. While a wider bandwidth in the FM signal increases the sharpness of the cross correlation peak, it also subjects the pulse to poor frequency resolution to track dispersive effects (Stergiopoulos and Ashley, 1997, "An experimental evaluation of split-beam processing as a broadband bearing estimator for line array sonar systems", J. Acoust. Soc. Am. 102: 0001-4966). Therefore a higher bandwidth remains beneficial up to a certain point. If the signal bandwidth is too large, the signal may not have sufficient resolution to map the dispersive properties of the interrogated medium and it may cause the method to break down. Equivalently, due to the poor signal to noise ratio that is an inherent property in the cross-correlation output of narrow bandwidth signals (Stergiopoulos and Ashley, 1997), it will be very difficult to recover the phase information associated with the dispersive effects of the interrogated medium. As a result, the bandwidth size of 0.5 MHz was selected empirically based on the minimum bandwidth required to produce a high signal to noise ratio cross correlation output and sufficient frequency resolution to map the dispersive properties.

The propagation time is estimated in two stages. In the first stage, cross correlation is performed to estimate the propagation time to within one period. The cross correlation process is described below. In the final stage, phase information of the received signal is used to improve the accuracy of the estimate, as described below.

Figure 7:
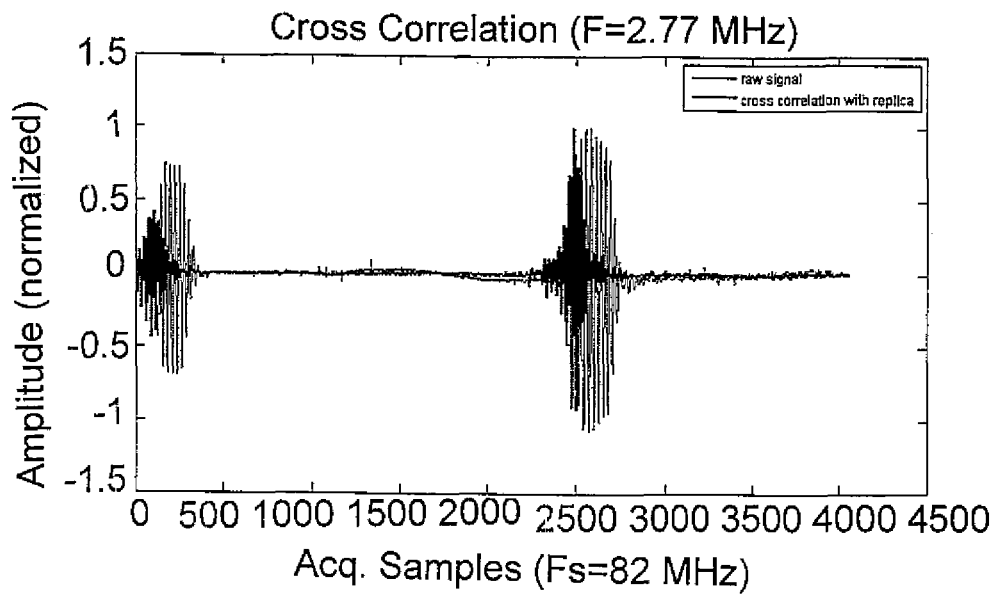
FIG. 7. Signal and cross correlation with replica.
Figure 8:
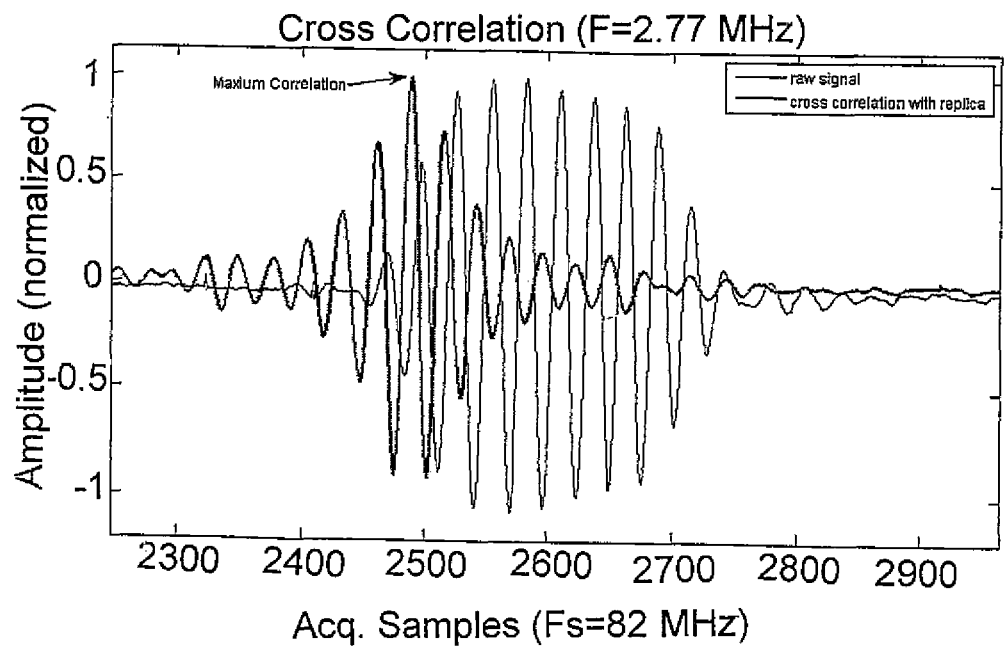
FIG. 8. Cross correlation with replica for received signal.
Figure 9:
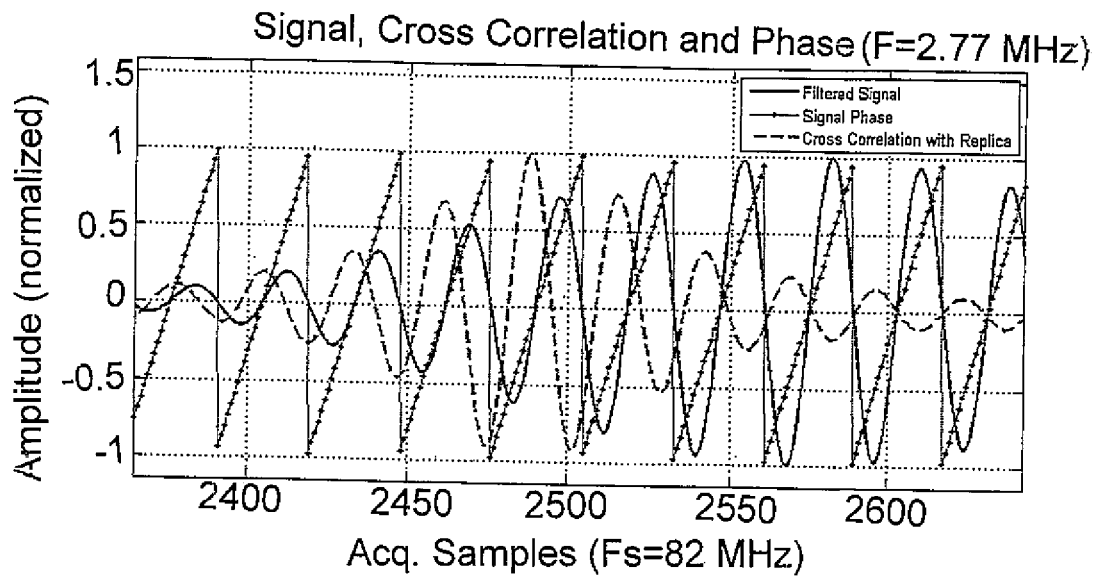
FIG. 9. Received signal, its instantaneous phase and cross correlation with replica.
Figure 10:
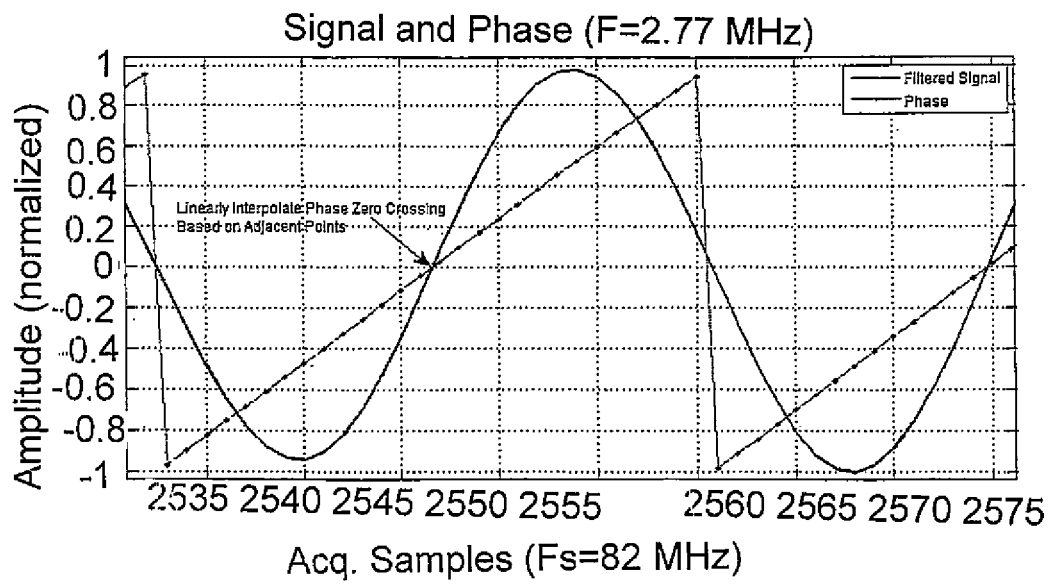
FIG. 10. Linear interpolation of phase zero crossing used for sub-sample time measurement.

Cross correlation processing (Bushong and Archer, 1991) is applied to the received signal by using as a replica the known characteristics of the transmitted signal, as shown in FIGS. 9 and 10. The replica for this correlation process can either be a stored sample of data that contains information about the transmitted signal as well as the transfer function of the system or it can be the transmitted signal itself (see FIGS. 7 and 8). The result of this correlation process yields a peak that marks the precise position in time that the signal is received by the Receiver, as depicted in FIGS. 7 and 8. Depending on the bandwidth of the replica, the pulse duration and the frequency characteristics of the transmitted signal, the waveform of the correlation peak can be noisy, which can degrade the accuracy of the time delay estimation process. One simple approach to minimize these noise effects on the cross-correlation output is to use FIR filters as discussed above and to apply a noise whitening filter, as defined in Bushong and Archer, 1991, and in the next sub-section.

After filtering the cross correlation output, its envelope is calculated using a Hilbert Transform. As will be apparent to one of skill in the art, the envelope identifies the peak of the correlation output more accurately, and therefore, it will provide a better estimate of the propagation time. The Hilbert Transform is therefore a second stage attempt to maximize the accuracy of the system to estimate the propagation time. The Hilbert transform is important in signal processing, where it is used to derive the analytic representation of a signal u(t). In signal processing, the analytic representation of a real-valued signal facilitates many mathematical manipulations of the signal. The basic idea is that the negative frequency components of the Fourier transform (or spectrum) of a real-valued function are superfluous, due to the Hennitian symmetry of such a spectrum. These negative frequency components can be discarded with no loss of information, providing one is willing to deal with a complex-valued function instead. As long as the manipulated function has no negative frequency components, the conversion from complex back to real is just a matter of discarding the imaginary part.

The analytical signal can also be expressed in terms of complex polar coordinates, where $$A(t) = |x_a(t)| = \sqrt{x^2(t) + \hat{x}^2(t)} \quad (10)$$

$$\phi(t) = \arg\{x_a(t)\} \quad (11)$$

are, respectively, the amplitude envelope and instantaneous phase of the signal. Both are required to get an approximate estimate of the received signal's time of arrival, Rx.

The peak of the cross correlation function's envelope provides an estimate of the propagation time which is accurate to within one period. Greater accuracy can be obtained by using the received signal's phase information, as described below.

If $R_{corr}(f)$ is the correlation output in the frequency domain, the result of the post filter $R_{pf}(f)$ can be described as:

$$R_{pf}(f) = W(f) \times R_{corr}(f) \quad (12)$$

where W(f) is a whitening filter defined below by Equation (13) (see Bushong and Archer, 1991). The inverse FFT of $R_{pf}(f)$ provides the cross-correlation time series $r_{pf}(t)$. Since estimates of W(f) are a function of the signal and noise spectra, the signal's coherence properties must either be known or estimated. The phase transform processor is a technique that uses only the cross spectral phase information and is defined by:

$$W(f) = |R_{corr}(f)|^{-1/2} \quad (13)$$

Cross correlation provides an estimate of the propagation time with a precision of one period. Greater accuracy is achieved by using the phase information of the received signal. First, filtering is performed on the received signal to improve the phase estimation, and then the phase is calculated by the Hilbert Transform. Specifically, linearity of the phase allows an interpolation process to be applied between sample points to obtain a more precise estimate of the propagation time, as shown in FIGS. 9 and 10.

The phase information, defined in Equation (10), has a relative offset of $\pi/2$ when calculated from the Hilbert transformation H. This constant offset can either be neglected due to the calculated difference or corrected as shown in (14).

$$\begin{aligned}\phi(t) &= \arg\{x_a(t)\} \\ &= \mathrm{atan}(\Im(x_a(t))/\Re(x_a(t))); \\ &= \mathrm{atan2}(\Im(H(x_a)), \Re(H(x_a))) - \pi/2; \\ &= \mathrm{atan2}(\Re(H(x_a)) - \Im(H(x_a)))\end{aligned} \quad (14)$$

$$\text{and } T_p = (x'_r - x'_t)/f_s$$

where $x_r$ and $x_t$ are the temporal samples of the received and transmit signals and $f_s$ is the sampling frequency. For any real arguments x and y not both equal to zero, atan 2(y, x) is the angle in radians between the positive x-axis of a plane and the point given by the coordinates (x, y) on it. The angle is positive for counter-clockwise angles (upper half-plane, y>0), and negative for clockwise angles (lower half-plane, y<0). To avoid different estimations between multiple measurements, it is best to stay as far away as possible from the discontinuities located at $-\pi/2$ and $+\pi/2$ and use the zero crossing as reference, and since the phase lines are linearly increasing, then it is possible to interpolate its value between sample points. Using this property, the time at which the phase line crosses zero during the cycle of interest is linearly interpolated using two adjacent sample points to obtain a high precision time stamp (see FIGS. 9 and 10). The process is repeated for both the transmitted and received signal at the marked signal periods, and the two time stamps are compared to calculate the precise time of propagation.

This procedure is repeated for all the other broadband signals centred at frequencies in the range of 500-KHz to 10-MHz. Then, the propagation time estimates for the different frequencies can be used to generate an ultrasonic fingerprint that reflects the dispersive properties of the interrogated medium.

The next step is to use this ultrasonic fingerprint to train a Neural Network. As demonstrated below, the DUS can be trained to identify and classify a medium on the basis of its dispersive characteristics.

Figure 5:
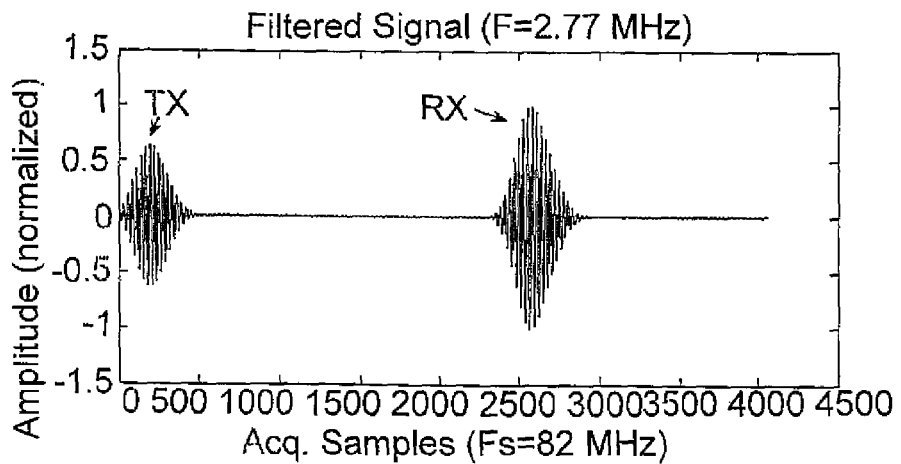
FIG. 5. Filtered transmit and received signals.
Figure 6:
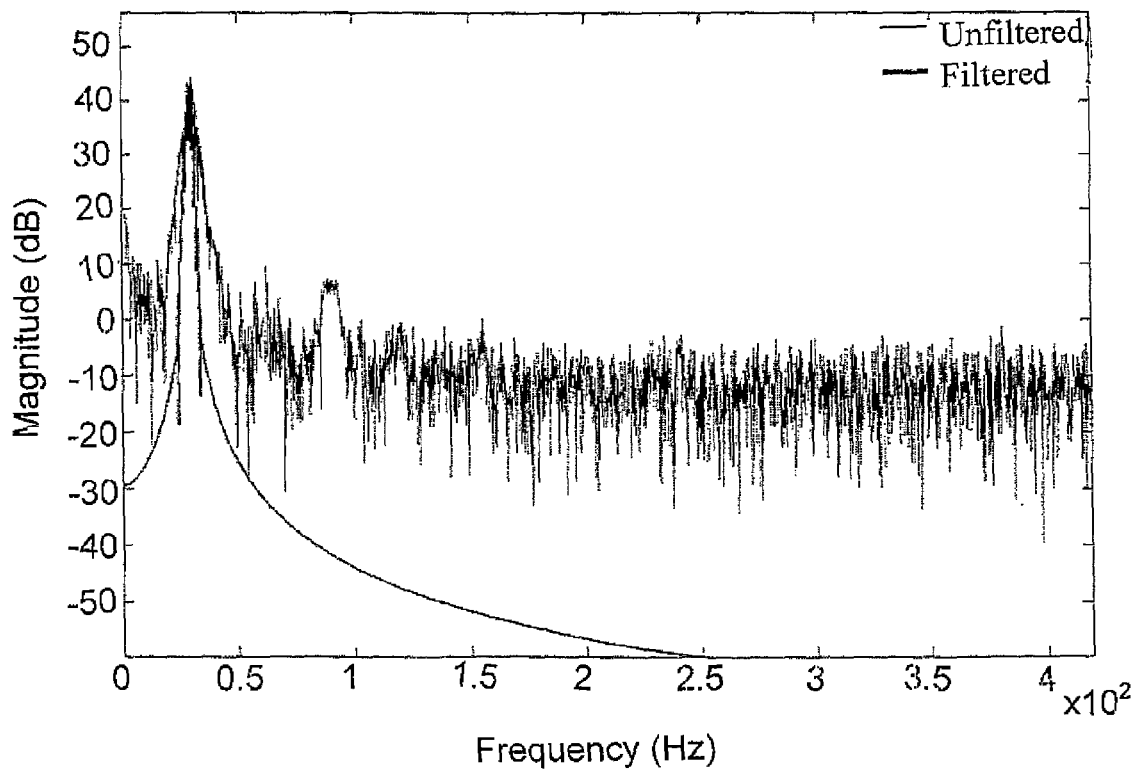
FIG. 6. Spectrum of filtered and unfiltered signals.

As stated previously, poor signal to noise ratio is the primary source of interference that can affect time delay estimates for the propagating signals in the medium of interest. To minimize the noise effects and improve the phase estimation process, a digital zero phase FIR or Infinite Impulse Response (IIR) filter was applied on the transmitted and received signals, as shown in FIG. 5. The advantage of an IIR filter is the lower computing requirements, but it also has a tendency to become unstable. A FIR filter is always stable but the required computational effort grows with higher orders and smaller bandwidths. Both have their advantages and one has to decide which architecture suits the current application. The filtered signal contains only a narrow band spectrum centred on the filter's band pass frequency regime. As an example, FIG. 6 shows the spectrum of the filtered and unfiltered signals. This filtering process improves the phase estimation process previously discussed.

A decision support system is essential when the dispersive properties of very similar media are being compared, as their dispersion patterns become difficult to distinguish for a human operator. In the current implementation, a Support Vector Machine (SVM) is used for the DUS as a decision support process. The SVM is a type of machine learning technique that is capable of being trained with known patterns in order to identify unknown patterns.

A Support Vector Machine executes an algorithm that classifies data into pre-defined categories based on prior information, or training. Conceptually, if classes of data, each with two variables per sample, are presented, each sample could be plotted on a two-dimensional plane. The SVM will attempt to create lines that maximally separate the classes. In some embodiments, the output of the DUS system comprises time delay estimates for different frequencies that represent the dispersive properties of a specific medium. For two slightly different media, the corresponding dispersive graphs at the output of the DUS system may almost look identical and neural networks (i.e. SVM processing) are the best way to identify their differences in order to classify them.

Figure 11:
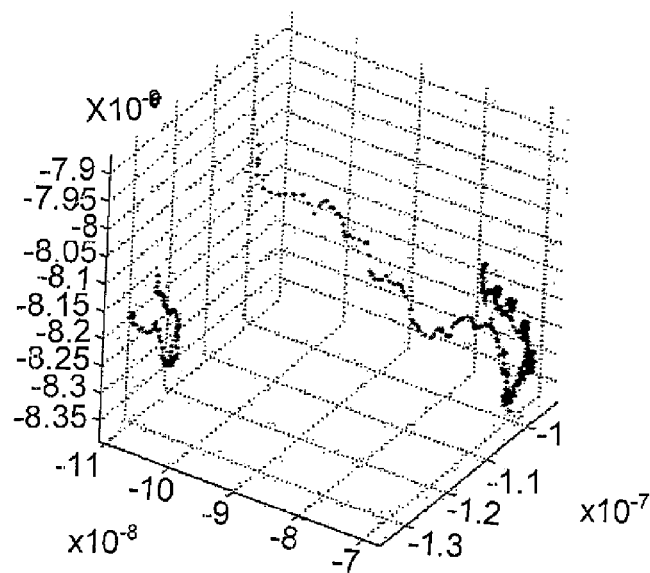
FIG. 11. Three-dimensional example of hyper-space sample distribution and classification.

In practice, data could contain more than two variables per sample. Data containing N variables would be effectively represented in an N-dimensional hyper-space (see FIG. 11). The support vector machine will attempt to create N−1 dimensional hyper-planes that maximally separate the different classes. When more than two classes are present, the SVM will repeat the process for all possible pairs, creating M(M−1)/2 hyper-planes, where M is the number of classes. While more difficult to visualize, hyper-planes are simple mathematical extensions of the two dimensional case.

During training, a large collection of data containing values and their associated classes are presented to the SVM. The machine constructs the hyper-planes that maximally separate different classes, and stores the separation planes' parameters in a model. Once complete, the model can be used to classify new data previously unseen by the SVM into one of the known categories.

As an example, the system could be trained to detect different type of saline solutions with concentrations of 5%, 10%, 15%. These would be treated as three categories. If the system analyzes a saline solution that is 14%, then it will interpret the data as being between 10% to 15% and will classify it as a 14% saline solution.

The dataset presented for training should optimally span a thoroughly representative range of possibilities for the particular class, that is, the N-dimensional cloud of data-points should fill as much of the true hyper-space volume relating to that class as possible. This will ensure SVM robustness so that interpolation or extrapolation for data beyond or in between training set data-points is minimized during classification.

Once training is complete and a model constructed, unknown data with the same dimension as the training set are fed into the model. Each unknown data point becomes another point in N dimensional space, and the SVM will compare the point's location to hyper-planes created during training to identify the class of the unknown sample based on its position relative to the hyper-planes.

In the example provided above, various concentrations of saline solution were analyzed. Taking that example further, if the DUS system has to classify a wide range of unknown saline solutions ranging between 5% to 50%, then the DUS system would need to be trained extensively with known samples of saline solutions covering the same range. Essentially, the more extensive the training of the system, the better the system will be at discriminating closely related mediums.

For the Dispersive Ultrasound System, dispersion patterns are stored in samples containing N variables, with N being the number of frequencies used. The SVM constructs hyper-planes in an N-dimensional space for classification of unknown samples.

As a complement to the machine learning approach to the diagnosis of internal brain injury from blast exposure, we have developed a simple simulation model of ultrasonic dispersion in intracranial tissues. The model takes into account the basic anatomical features of the skull and intracranial space, as well as the acoustic dispersion arising from the relevant tissues, to permit simulation and study of dispersion spectra. The model is an aid to better understand observed variations in dispersion spectra, and to assess possible performance limitations of the machine learning approach.

In clinical applications for the present Dispersive Ultrasound invention, the transmitting and receiving transducers are placed bilaterally on the temples. The acoustic signal traverses the tissues between the transducers. As such, the acoustic propagation path consists of a series of tissue layers that are roughly symmetric about the midpoint. The model makes a linear dispersion approximation, in which the propagation speed of the ultrasonic wave changes linearly with frequency:

$$c(f) = c(f_o) + (f - f_o)\Delta \qquad (15)$$

The dispersion trend $\Delta$ is tissue-specific, as are the reference values $f_o$ and $c(f_o)$. The linear approximation is justifiable for the limited frequency range relevant to our system, and the few measurements of acoustic dispersion in biological tissues that are available generally assume linear dispersion in any case (Kremkau et al., 1981, "Ultrasonic attenuation and propagation speed in normal human brain", J. Acoust. Soc. Am. 70: 29-38; Fry and Berger, "Acoustical properties of the human skull", J. Acoust. Soc. Am. 63: 1576-1590; Duck, 1990, Physical Properties of Tissue: A Comprehensive Reference Book, Academic Press). If warranted by operational requirements and justified by the availability of suitable data, the model could be easily generalized to include non-linear dispersion curves. At the present time, the model does not include simulation of all of the tissues and fluids present along the acoustic propagation path. This is because data on the dispersive characteristics of certain tissues are not available in the published literature; were data to become available, it could be readily incorporated into the model. In its present form the model includes the tissues that account for approximately 90% of the total propagation path length.

As an example, a DUS system is trained to distinguish between traumatic injuries due to concussion and blast exposure. As will be apparent to one of skill in the art, the biological differences of closely related brain injuries are biologically very minor. Furthermore, although both type of brain injuries may be treated in the same way, there are fundamental differences between them regarding the kind of inflammatory response that they induce in the brain. For example, when a concussion is treated properly and the patient is not exposed to more concussions, the patient may recover after a certain period. However, for traumatic brain injury due to a blast, it has been clinically observed in soldiers returning from Iraq and Afghanistan that their brain inflammatory response expands and gets worse over time. Therefore, a DUS system, when trained well to cover cases of concussion and injuries due to blasts (TBI), can be a valuable diagnostic system to distinguish between the different stages of either concussion or TBI and their progression (i.e., whether they get better or worse). Specifically, these are differences in the dispersion properties of the brain tissues when exposed to concussion or blast effects. Furthermore, these differences result in fundamental diagnostic properties that the DUS can detect while methods such as CT and MRI cannot provide the same discriminatory capability.

in another example, an intracranial hematoma could be modeled by the displacement of certain tissues by a layer of blood along the propagation path; the impact of the hematoma upon the dispersion spectrum could then be evaluated.

Figure 12:
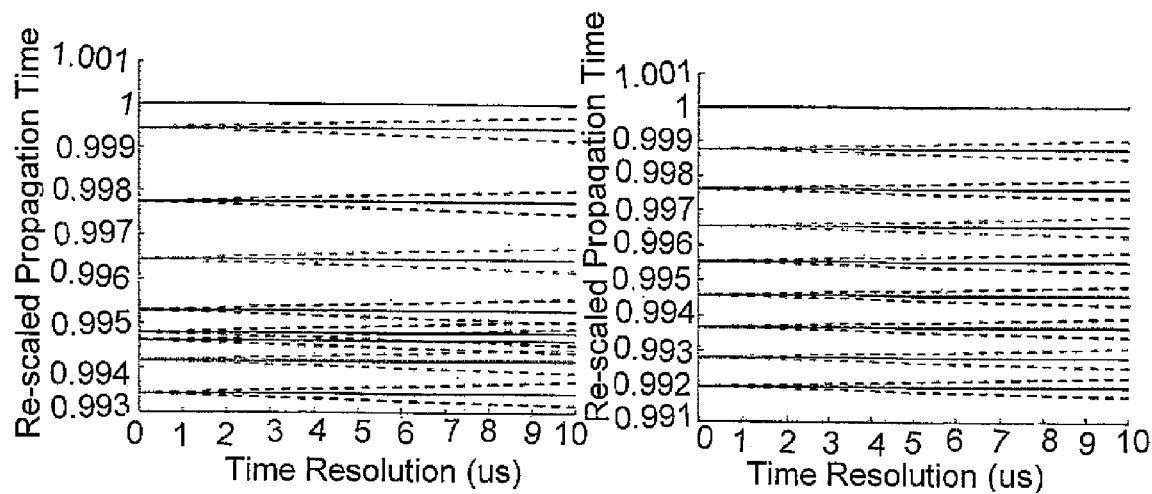
FIG. 12. Uncertainties in the propagation times induced by time-resolution limits in the Dispersive Ultrasound System. The dashed lines indicate the range of uncertainty in the propagation time as a function of the system's time resolution. The propagation times are normalized with respect to the frequency having the longest propagation time. The left-hand side shows a randomly selected frequency set in the range of 0-5 MHz; the right hand side shows a frequency set in the same range, but with a 0.4 MHz inter-frequency spacing to avoid overlap of the uncertainty bands resulting from the finite time resolution of the device.

The model is a tool that permits greater insight into the problem space than is provided by a machine learning system alone. For example, the limited time resolution of the Dispersive Ultrasound System induces an uncertainty in the measurements of propagation times that appears as a noisy fluctuation centred around a mean value. The effects of these uncertainties on the dispersion spectrum can be modeled, as in FIG. 12. If the ultrasound frequencies interrogating the medium are too closely spaced, as in the left-hand side of FIG. 12, the ordering of the propagation times can be unstable, which adversely affects the performance of a machine learning system. Specifically, the space between lines should be sufficiently wider than the error-noise fluctuation of the system, which depends on the signal-to-noise ratio characteristics of a DUS system. To define this space, it is a matter of calibrating the system to define its specific discriminatory capabilities based on the signal quality. The model can be used to select a set of frequencies, as in the right-hand side of FIG. 12, for which the inter-frequency spacing is large enough that the time-resolution uncertainties do not introduce ordering ambiguities.

There are numerous other uses to which the Intracranial Dispersion Model can be put. It can, for instance, help us to understand the observed changes in dispersion spectra in response to certain changes in the insonified medium; it can clarify which (of the represented) tissues have the greatest impact on the dispersion spectrum; and it can give insight into the accuracy with which a machine learning system succeeds in classification tasks.

Two other experiments were conducted using the DUS. The purpose of these experiments was to test the feasibility of using dispersion to discriminate between similar media, and to assess the suitability of a machine learning approach to medium identification.

The first experiment attempted to classify different types of off-the-counter juices (i.e. Apple, Grape, Orange, etc.) on the basis of their ultrasound dispersion patterns. The second was a quality control experiment in which ultrasound dispersion patterns were used to identify juices of unacceptable quality because of dilution.

Surprisingly, the viscosities and densities of some of the above juices were almost identical. The DUS system however detects the differences in the scattering properties of the molecular structures of the juices that are defined by their dispersive properties. For example, for two different fluids with identical densities and very similar molecular structures, the system will have difficulties detecting their differences. On the other hand, for a saline versus a glucose solution, it was easy for DUS to discriminate them because of their different molecular structures which generate different ultrasound scattering properties.

The experiments were conducted to measure the DUS' functionality, sensitivity, robustness and stability. In the first experiment, different media of highly similar consistency, density, and viscosity were tested in order to determine if the DUS was capable of performing its primary function of media classification, and to see if it was sensitive enough to distinguish between highly similar media. In the other experiment, the same medium, from different batches and with different level of dilution, was tested over several weeks' time span. This measured the system's functionality in quality control applications, the decision support system's robustness to variations over batches and time, and the system's long term stability over several weeks.

The ultrasound probes (i.e. transmitter and receiver) were affixed to opposite sides of a top-open cylindrical container measuring approximately 10 cm in height and 5 cm in radius, at approximately 5 cm from the bottom. An actively cooled water bath system was used to provide temperature control. A manually operated digital temperature probe was used during all experiments to measure both bath and medium temperatures.

The temperature of the media being studied with the DUS and the dimensions of the container both directly affect the ultrasound propagation times. Temperature directly affects the density of any fluid and density directly affects ultrasound propagation speed, as in Equation (1). Changes in medium temperature effectively multiply the dispersion pattern by a coefficient with magnitude proportional to $p_o^{-1/2}$. Similarly, since the DUS measures propagation time, a change in distance between transmitting and receiving probes also multiplies the dispersion pattern by a value proportional to the change in distance.

Both training and testing data were recorded in 3 sets of frequency sweeps, each sweep containing 12 frequencies in the range of 0.5 MHz to 10 MHz. Testing data were recorded in the same way as training data because this allowed testing data to be used in training if it became necessary. Temperature was varied between 8° C. to 20° C. during data acquisition for both experiments except for the juice-box test dataset.

Different types of off-the-shelf juice boxes were obtained and data was acquired separately for each box. The boxes were divided into two groups: training group and testing group. The training group was used to acquire data used to train the system for classification and the test group was used to test the classification success rate.

The training group of juices were individually prepared and submerged in the temperature controlled water bath as described above and raw data was acquired. During acquisition, the temperature of the medium was incrementally increased, eventually reaching room temperature.

The testing groups of juices were individually prepared in the same way as the training group. Temperature was not varied during data acquisition; rather data was acquired for three different fixed temperature levels at approximately 10° C., 15° C. and 20° C.

Figure 13:
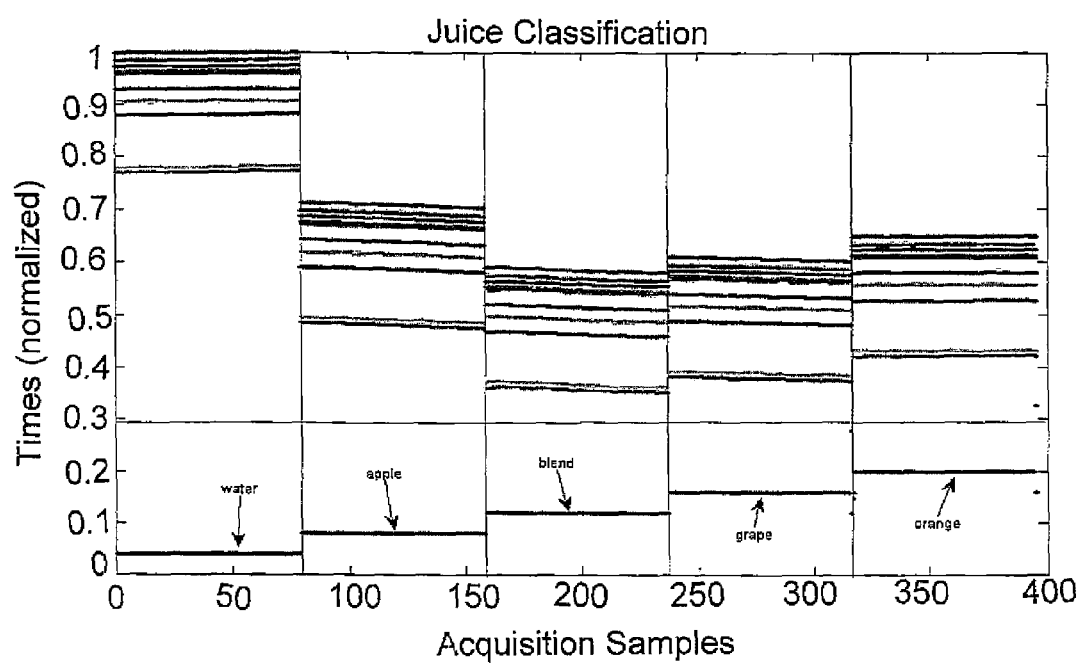
FIG. 13. Data used for testing Support Vector Machine (SVM) results. Line colour represents frequencies. The vertical axis is normalized propagation time and the horizontal axis is acquisition number. The black lines at the bottom are SVM output representing the SVM-identified classes associated with the data above. Classification was 99% successful.

Frequency-propagation time information was calculated and the timing information was fed into the SVM algorithm of the decision support system. The classification results of the testing set were compared with knowledge of the actual medium content to verify success rate. FIG. 13 shows the results from the Juice Classification Experiment.

Double-blind experiments were conducted in which cranberry juice samples were divided into three groups: Acceptable, Unacceptable and Unknown. Within each group, 4 samples were provided, with the unknown group containing samples of both Acceptable and Unacceptable types. The unknown group samples were similar to, but not exactly the same as, the samples in the known group. The objective of the experiment was to classify the unknown samples based on data acquired with the known samples.

Data was acquired for each sample using the methods outlined above. The timing information for the known samples was used to train the SVM, and then the unknown samples were classified.

Figure 14:
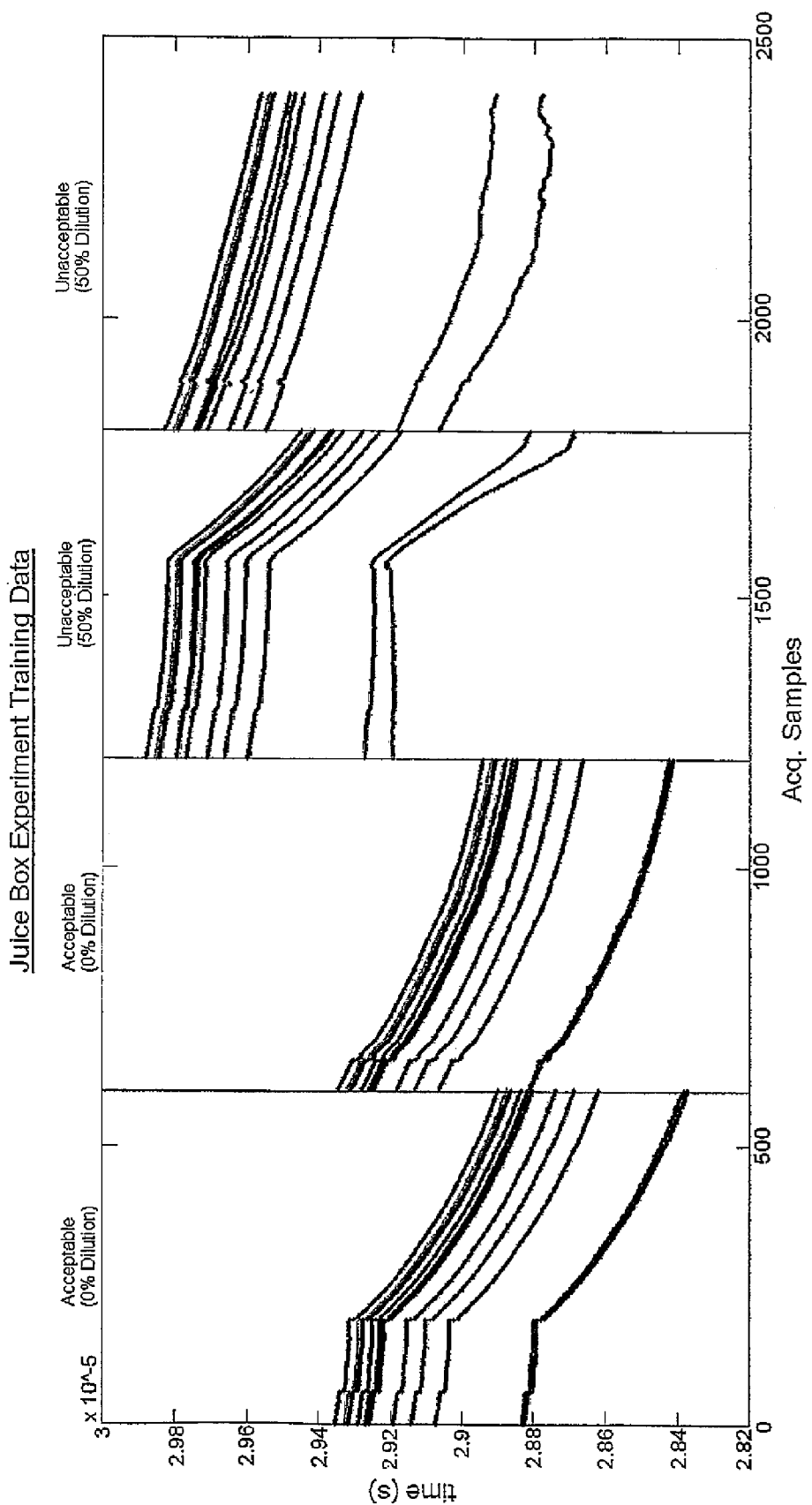
FIG. 14. Training data for the quality control experiment. Coloured lines represent different frequencies. The vertical axis is propagation time and the horizontal axis is acquisition number. All acquisitions and their associated groups are input into the SVM during training. Temporal ordering has no effect on training results.
Figure 15:
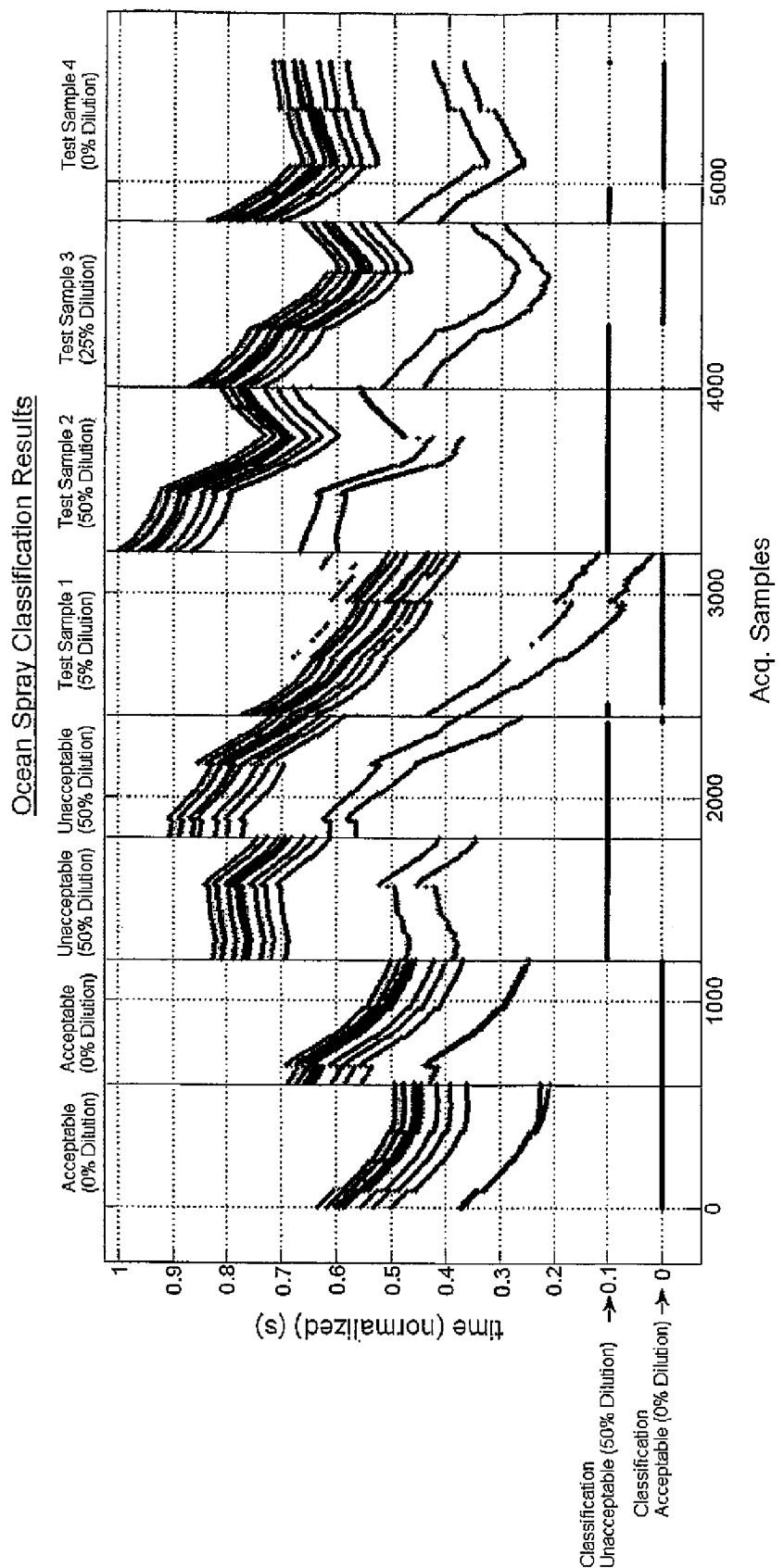
FIG. 15. Data used for testing and SVM results. Line color represents frequencies. The vertical axis is the normalized propagation time and the horizontal axis is acquisition number. The black lines at the bottom are the SVM output representing the SVM-identified classes associated with the data above.

Experiment results were divided into two types: visual dispersion pattern results, and classification results produced by the decision support system based on the dispersion pattern. While the visual dispersion patterns are more intuitive to understand, simple visual inspection often does not have sufficient resolution or consistency for making correct classifications, although visual inspection can often make judgments on the system's stability. Classification results are produced by the decision support system based on numerical data used to generate the visual dispersion patterns, as depicted in FIGS. 14 and 15. The decision support system is sensitive to subtle features of the dispersion pattern and therefore is able to distinguish patterns that appear to be similar under visual inspection.

These experiments successfully verified the functionality and performance of the DUS in dispersion measurement and medium classification applications.

In the juice classification experiment, it was seen that the dispersion patterns of different juices were almost identical upon visual inspection. Classification results from this experiment demonstrated that the system was nonetheless able to identify each type of juice with good reliability, as depicted in FIG. 13. This is a complex graph as its upper part presents the dispersive properties of the different mediums while the lower part shows the classification results (output of the neural network processing) of the DUS system which demonstrates its discriminatory capability to distinguish the different fluids. This indicated that the decision support system functioned correctly, and that the system had sufficient sensitivity and resolution to allow the decision support system to differentiate between visually similar dispersion patterns.

In the quality control experiment, the dispersion patterns of known "Acceptable" and "Unacceptable" (dilute) samples were visually distinguishable, as shown in FIG. 14, but it can be seen from the test samples that there were sometimes disagreements between the visual classification pattern and the decision support system results for the unknown samples, as shown in FIG. 15. For the blind test, the classification results for the unknown samples were verified to be correct, although the dilution factors for the unknown samples was different than those of the known samples, as shown in FIGS. 14 and 15. This set of experiments indicated that the DUS is sufficiently robust to classify dispersion patterns in the presence of variations in the quality level of the known and unknown samples. Furthermore, the quality control experiment was conducted over several weeks, and classification results remained consistent for data taken at the beginning (Acceptable 1) and near the end of several weeks later (Test Sample 4), which verified the system's long term stability against temperature drifting and aging in the electronic components or ultrasound transducer.

As will be appreciated by one of skill in the art, long term stability is a very critical property. Specifically, stability ensures that the system detects the diagnostic or quality control cases and compares them with a training data base. If the long-term stability was not there then the system would have to be trained very frequently. In some cases, as in the diagnostic cases for concussion or Traumatic Brain Injury (TBI), this may not be possible.

The SVM naturally becomes more robust and less sensitive to noise when more frequencies are available, as each additional dimension adds more degrees of freedom for the classification hyper-plane. It has been observed that in the presence of large variations in propagation time of 1 or 2 frequencies for the same medium, the SVM was still able to correctly classify the medium based on the remaining stable frequencies (FIG. 15). This indicates that the SVM does not require a match in all frequencies for classification, and also reinforces the expectation that additional frequencies increase system robustness.

We have described a portable, low-cost system that uses the dispersive properties of ultrasonic waves to identify and characterize the insonified medium as discussed above.

The Dispersive Ultrasound System (DUS) is comprised of a data acquisition system (ultrasonic transmitting and receiving transducers), a signal processing process, and a decision support system. We have described all three components, with an emphasis on the signal processing. We have also described a set of laboratory experiments that illustrated the utility of the dispersive ultrasound invention for probing the properties of a medium. With a Support Vector Machine (SVM) decision support system, the DUS was able to distinguish fluids with similar dispersion patterns, even when those patterns were difficult to distinguish by visual inspection. This demonstrates that the system is sensitive enough to detect subtle dispersive changes such as might result from injury to intracranial tissues following blast exposure.

While the preferred embodiments of the invention have been described above, it will be recognized and understood that various modifications may be made therein, and the appended claims are intended to cover all such modifications which may fall within the spirit and scope of the invention.

REFERENCES

Stergios Stergiopoulos, Andreas Freibert, Jason Zhang, Dimitrios Hatzinakos, "Non-invasive monitoring of vital signs and traumatic brain injuries", Defence R&D Canada—Toronto, Department of National Defence, (Technical Report), DRDC Toronto, TR 2008-105, July 2008.

Stergiopoulos S. and Wrobel M. "Non-Invasive Diagnostic Ultrasound System Monitoring Brain Abnormalities", U.S. patent application Ser. No. 10/898,208, (DND File No. 1416-011007 USA), July 2003

Stewart C. Bushong and Benjamin R. Archer, "Diagnostic Ultrasound", Mosby Inc., 1991.

Stergios Stergiopoulos and Anthony T. Ashley, "An experimental evaluation of split-beam processing as a broadband bearing estimator for line array sonar systems", J. Acoust. Soc. Am. 102 (6), 0001-4966, December 1997.

F. W. Kremkau, R. W. Barnes, and C. P. McGraw, "Ultrasonic attenuation and propagation speed in normal human brain", J. Acoust. Soc. Am. 70 (1), 29-38, 1981.

F. J. Fry and F. E. Berger, "Acoustical properties of the human skull", J. Acoust. Soc. Am. 63 (5), 1576-1590.

F. A. Duck, Physical Properties of Tissue: A Comprehensive Reference Book, Academic Press (1990).

The invention claimed is:

1. A method of classifying a medium comprising:
   a) placing a transmitting transducer and a receiving transducer on opposite sides of a medium and traversing the medium with a plurality of frequency modulated ultrasound pulses between the transducers, each pulse being transmitted at a different frequency;
   b) identifying, with a computer, a signal from one of the ultrasound pulses received by the receiving transducer by pulse duration, center frequency and bandwidth;
   c) estimating propagation time through the medium for said signal using cross correlation with a replica of the transmitted pulse using the computer;
   d) improving the estimate of the propagation time by determining when the phase of said signal changes sign by performing an interpolation based on a linear portion of the phase using the computer;
   e) repeating steps (b)-(d) for each frequency of the plurality of ultrasound pulses;
   f) using information derived from the plurality of ultrasound pulses to generate a dispersion pattern of the medium using the computer; and
   g) using the computer to classify the medium based on characteristics of the dispersion pattern.

2. The method according to claim 1 including at step (b) applying a temporal window to one of the signals.

3. The method according to claim 1 wherein each pulse of the plurality of ultrasound pulses has a bandwidth of 0.5 MHz.

4. The method according to claim 1 including applying Finite Impulse Response (FIR) filters when estimating the propagation time.

5. The method according to claim 1 wherein when the phase of said signal changes sign is calculated by Hilbert transformation.

6. The method according to claim 1 wherein the dispersion pattern is compared to a database of dispersion patterns of known media and the medium is classified based on said comparison.

7. The method according to claim 6 wherein the database comparison is carried out by a support vector machine.

8. The method according to claim 1 wherein the medium is intracranial tissues.

9. The method according to claim 8 wherein frequencies of the plurality of ultrasound pulses are between 500 kHz and 10 MHz.

10. The method according to claim 8 wherein the medium is intracranial tissues which are suspected of having been altered by a brain injury.

11. The method according to claim 10 wherein frequencies of the plurality of ultrasound pulses are between 500 kHz and 10 MHz.

* * * * *